US006971999B2

(12) United States Patent
Py et al.

(10) Patent No.: US 6,971,999 B2
(45) Date of Patent: Dec. 6, 2005

(54) INTRADERMAL DELIVERY DEVICE AND METHOD

(75) Inventors: Daniel Py, Stamford, CT (US); Julian V. Chan, Spring Valley, NY (US)

(73) Assignee: Medical Instill Technologies, Inc., New Milford, CT (US)

( * ) Notice: Subject to any disclaimer, the term of this patent is extended or adjusted under 35 U.S.C. 154(b) by 212 days.

(21) Appl. No.: 10/294,926

(22) Filed: Nov. 14, 2002

(65) Prior Publication Data

US 2003/0093032 A1 May 15, 2003

Related U.S. Application Data

(60) Provisional application No. 60/332,694, filed on Nov. 14, 2001.

(51) Int. Cl.[7] .............................................. A61M 5/00
(52) U.S. Cl. ...................................... 604/115; 604/181
(58) Field of Search ............................ 604/65, 67, 154, 604/189, 207, 208, 209, 211, 181, 136, 198, 604/263, 192, 272, 268, 264, 167, 180, 244, 604/117; 128/DIG. 11, 12

(56) References Cited

U.S. PATENT DOCUMENTS

| 1,934,046 | A | | 11/1933 | Demarchi |
| 2,876,770 | A | | 3/1959 | White |
| 3,400,715 | A | | 9/1968 | Pederson |
| 3,672,368 | A | | 6/1972 | Schwarz |
| 3,896,810 | A | * | 7/1975 | Akiyama .................... 604/117 |
| 3,905,375 | A | | 9/1975 | Toyama |
| 3,920,001 | A | | 11/1975 | Edwards |
| 4,299,219 | A | | 11/1981 | Norris, Jr. |
| 4,373,526 | A | | 2/1983 | Kling .......................... 128/215 |
| 4,393,870 | A | | 7/1983 | Wagner |
| 4,537,593 | A | | 8/1985 | Alchas |
| 4,574,965 | A | | 3/1986 | Meierhoefer |
| 4,600,403 | A | | 7/1986 | Wagner |
| 4,690,675 | A | | 9/1987 | Katz |
| 4,723,940 | A | | 2/1988 | Wiegerinck |
| 4,787,891 | A | | 11/1988 | Levin et al. |
| 4,850,996 | A | | 7/1989 | Cree |
| 4,861,341 | A | | 8/1989 | Woodburn |
| 4,886,499 | A | | 12/1989 | Cirelli et al. |
| 4,892,107 | A | | 1/1990 | Haber |

(Continued)

FOREIGN PATENT DOCUMENTS

WO    WO95/01198    1/1995

(Continued)

*Primary Examiner*—Manuel Mendez
(74) *Attorney, Agent, or Firm*—McCarter & English, LLP (57) ABSTRACT

The subject intradermal delivery device provides for penetration to a fixed depth without requiring special expertise by the user. The device consists of a syringe nested inside an inner shell and an outer shell. An elongated annular channel is formed between the inner shell and the outer shell. A housing receives the syringe and concentric shells in a sliding engagement. A first seal on the distal end of the housing forms a variable length channel in communication with the elongated annular channel via a port formed in the outer shell. When the device is applied to the skin, the housing and syringe are slid towards the skin, and the variable length channel generates a vacuum which forces the skin to bulge into the elongated annular channel. As a result, the skin is tensioned across the inner shell to form a substantially planar, taut target area of skin. The taut target area of skin in combination with a stop on the housing determines the insertion depth of the syringe.

27 Claims, 11 Drawing Sheets

U.S. PATENT DOCUMENTS

| | | |
|---|---|---|
| 5,057,089 A | 10/1991 | Greco |
| 5,092,376 A | 3/1992 | Blankenship et al. |
| 5,281,205 A | 1/1994 | McPherson |
| 5,306,258 A | 4/1994 | de la Fuente |
| 5,358,489 A | 10/1994 | Wyrick |
| 5,364,362 A | 11/1994 | Schulz |
| 5,385,561 A | 1/1995 | Cerny |
| 5,514,097 A | 5/1996 | Knauer |
| 5,527,297 A | 6/1996 | Paul |
| 5,531,706 A | 7/1996 | de la Fuente |
| 5,599,309 A | 2/1997 | Marshall et al. |
| 5,709,662 A | 1/1998 | Olive et al. |
| 5,709,668 A | 1/1998 | Wacks |
| 5,728,074 A * | 3/1998 | Castellano et al. ......... 604/207 |
| 5,873,856 A | 2/1999 | Hjertman et al. ........... 604/117 |
| 5,957,897 A | 9/1999 | Jeffrey |
| 6,093,170 A | 7/2000 | Hsu et al. |
| 6,139,526 A | 10/2000 | Bedner et al. |
| 6,149,629 A | 11/2000 | Wilson et al. |
| 6,159,185 A | 12/2000 | Tanihata |
| 6,171,284 B1 | 1/2001 | Kao et al. |
| 6,186,982 B1 | 2/2001 | Gross et al. |
| 6,200,291 B1 | 3/2001 | Di Pietro |
| 6,221,056 B1 | 4/2001 | Silverman |
| 6,231,550 B1 | 5/2001 | Laughlin |
| 6,319,234 B1 | 11/2001 | Restelli et al. |
| 6,322,540 B1 | 11/2001 | Grabis et al. |
| 6,332,875 B2 | 12/2001 | Inkpen et al. |
| 2001/0011170 A1 | 8/2001 | Davison et al. |
| 2001/0012925 A1 | 8/2001 | Alchas |
| 2001/0056263 A1 | 12/2001 | Alchas et al. |
| 2002/0010423 A1 | 1/2002 | Gross et al. |
| 2002/0013602 A1 | 1/2002 | Huttner |
| 2002/0038111 A1 | 3/2002 | Alchas et al. |
| 2002/0045866 A1 | 4/2002 | Sadowski et al. |

FOREIGN PATENT DOCUMENTS

| | | |
|---|---|---|
| WO | WO99/34850 | 7/1999 |

* cited by examiner

INTRADERMAL DELIVERY DEVICE AND METHOD

CROSS-REFERENCE TO RELATED APPLICATION

This application claims priority to U.S. Provisional Patent Application No. 60/332,694, filed Nov. 14, 2001, which is incorporated herein by reference.

BACKGROUND OF THE INVENTION

1. Field of the Invention

The subject invention relates to instruments and methods for injecting a substance into a person or animal, and more particularly to an improved instrument and method for injecting the substance intradermally.

2. Background of the Related Art

Drug delivery into the soft tissue inside the dermis, i.e., intradermal delivery, with a very small needle has been shown to slow drug release time and reduce or eliminate nerve ending stimulation and hence patient reaction. The challenge to delivering drugs in this fashion includes the need for precise control over needle penetration depth which can vary due to tissue compliance, penetration angle and the skill level of the person conducting the injection.

In view of the above, several systems have been developed to aid in the intradermal delivery of substances. An example is illustrated in U.S. Pat. No. 6,200,291 to Di Pietro which is incorporated herein by reference in its entirety. Di Pietro shows a device 1 controlling the penetration depth of a needle. The device 1 has a body 5 with a tapered portion 2 surrounding a needle 3. As the tapered portion 2 is pressed against the skin 8, the skin 8 is slightly deformed in order to allow the needle 3 to enter the skin a set length. Microholes 7 in the body 5 prevent vacuum accumulation and allow easy removal of the device 1. Another example is U.S. Pat. No. 1,934,046 to Demarchi which is incorporated herein by reference in its entirety. Demarchi is directed to a syringe 1 surrounded by a glass bell 3. The glass bell 3 is sealingly engaged to a flexible bulb 5. In use, the bulb 5 is depressed and the mouth of the bell 3 is placed against the skin. Relaxing the bulb creates a negative pressure which draws the skin upwardly into the bell 3 and into engagement with the needle 2 for injection. To remove the syringe 1, the bulb 5 is depressed a second time to reverse the negative pressure.

Still another example is U.S. Pat. No. 4,299,219 to Norris, Jr. which is incorporated herein by reference in its entirety. Norris, Jr. shows a device 10 for inserting a cannula 42 in a vein. A vacuum cylinder 11 surrounding the cannula 42 terminates in an oblique opening which is surrounded by a soft gasket 15. A vacuum syringe 13 is sealingly engaged to the cylinder 11 for creating negative pressure in the vacuum cylinder 11. In operation, the gasket 15 is placed over the desired vein and the vacuum syringe 13 creates negative pressure within the cylinder 11. As a result, a localized distension of the skin and underlying vein causes engorgement into that area of the vein to facilitate successful insertion of the cannula 42.

However, there are problems associated with these devices. Each of these devices varies in penetration depth and angle dependent upon the skill of the user. Pain and discomfort for the recipient also vary with the skill of the user. There is a need, therefore, for an improved device and method which repeatably provides a definite relative skin state for precise needle penetration and reduced patient reaction.

SUMMARY OF THE INVENTION

One aspect of the present invention is directed to an intradermal delivery device including an inner shell and a needle for delivering a substance, wherein the needle is slideably engaged within the inner shell and biased in a retracted position. An outer shell is concentric with the inner shell and an elongated annular channel is defined therebetween. A housing slideably receives the outer shell, inner shell and needle, and defines a sealed channel of variable size in communication with the elongated annular channel. In the retracted position, the shells are placed against the patient's skin and the housing slides to increase the sealed channel in size, thereby creating a vacuum within the elongated annular channel. As a result, the vacuum engages the skin resulting in tensioning the patient's skin across the inner shell such that a reference plane is established with respect to the needle for injection thereof at a predetermined depth and release of the substance.

According to another aspect of the present invention, the delivery device comprises a housing including a base defining a first skin-engaging surface portion forming a needle aperture and defining a substantially planar target penetration region of skin, and a second skin-engaging surface portion extending radially relative to the first skin-engaging surface portion to substantially prevent relative movement of the skin and the base and releasably secure the base to the skin. A syringe of the device includes a syringe body coupled to the housing, a plunger slidably received within the syringe body, and a needle in fluid communication with the syringe body. The needle is movable through the needle aperture upon slidably moving the syringe through the housing, to thereby insert the needle into the substantially planar target penetration region of the skin and inject a substance contained within the syringe. A stop surface is fixed relative to a portion of the first skin-engaging surface and adapted to cooperate with the syringe to limit a depth of insertion of the needle into the substantially planar target penetration region of the skin.

According to another aspect of the present invention, a method for delivering a substance into a patient comprises the following steps:

(a) Providing a delivery device including a housing having a base defining a first skin-engaging surface portion forming a needle aperture and defining a substantially planar target penetration region of skin, and a second skin-engaging surface portion extending radially relative to the first skin-engaging surface portion to substantially prevent relative movement of the skin and the base, and releasably secure the base to the skin;

(b) Reciprocally mounting a syringe in the housing, wherein the syringe includes a syringe body for storing a substance, a plunger slidably received within the syringe body, and a needle in fluid communication with the syringe body;

(c) Releasably securing the first and second skin-engaging surface portions on the skin of the patient;

(d) Forming the substantially planar target penetration region of the skin within an area defined by the first skin-engaging surface portion;

(e) Inserting the needle of the syringe into the substantially planar target penetration region of the skin upon slidably moving the syringe through the housing;

(f) Controlling a depth of insertion of the needle into the substantially planar target penetration region with a stop surface fixed relative to the first skin-engaging surface for determining the depth of insertion in cooperation with the syringe; and (g) Injecting the substance from the syringe body through the needle into the patient.

One advantage of the present invention is that the needle may accurately be inserted a predetermined distance into a patient for injection of a substance therein.

Other advantages of the present invention will become apparent in view of the followed detailed description of preferred embodiments, claims, and accompanying drawings.

BRIEF DESCRIPTION OF THE DRAWINGS

So that those having ordinary skill in the art to which the disclosed invention appertains will more readily understand how to make and use the same, reference may be had to the drawings wherein.

DETAILED DESCRIPTION OF THE PREFERRED EMBODIMENT

The present invention overcomes many of the prior art problems associated with instruments for intradermally injecting substances. The advantages, and other features of the invention disclosed herein, will become more readily apparent to those having ordinary skill in the art from the following detailed description of certain preferred embodiments taken in conjunction with the drawings which set forth representative embodiments of the present invention and wherein like reference numerals identify similar structural elements.

Referring to FIGS. 1A through 1D, the subject device, referred to generally by reference numeral 110, provides for automatic needle orientation, penetration to a fixed depth, and then withdrawal in a single motion. After use, the device 110 can be reloaded for subsequent use. The device 110 comprises a needle syringe 112 nested inside two concentric shells, an inner shell 114 and an outer shell 116. An elongated annular channel 120 is formed between the inner shell 114 and the outer shell 116. Preferably, the syringe 112 engages the inner shell 114 in a friction fit which is fixed but not permanent as is well known to those of ordinary skill in the pertinent art. A housing 118 receives the concentric shells 114, 116 in a sliding engagement. A first seal 122 on the distal end of the housing 118 forms a variable length channel 123 in communication with the elongated annular channel 120 via ports 124 formed in the outer shell 116. It is envisioned that a single port 124 or a plurality of ports 124 may be used. A second seal 126 provides for airtight engagement of the proximal end of the concentric shells 114, 116 with the housing 118. A cap 140 threadably engages the housing 118 to selectively allow access within the housing 118 to replace the needle syringe 112 after use. In a preferred embodiment, a removable safety cap 121 prevents accidental sticks.

In a preferred embodiment, the needle syringe 112 has a body 128 defining a cavity 130 for storing the drug. A plunger 132 with a seal 134 slideably penetrates the body 128 for forcing the drug into the needle portion 136 and expelling the drug out the cannula (or needle) 137. As shown, when filled with a drug and in a retracted position, a portion of the body 128 extends within the housing 118. Preferably, a spring 138 biases the body 128 into the housing 118. It is envisioned that the biasing of the body 128 may be achieved by pneumatic, hydraulic and like means as would be appreciated by one of ordinary skill in the pertinent art based upon review of the subject disclosure. The cap 140 of the housing 118 secures a spring 142 about the plunger 132 such that as the cap 140 is depressed, the spring 142 slides along the plunger 132.

Figure 1A:
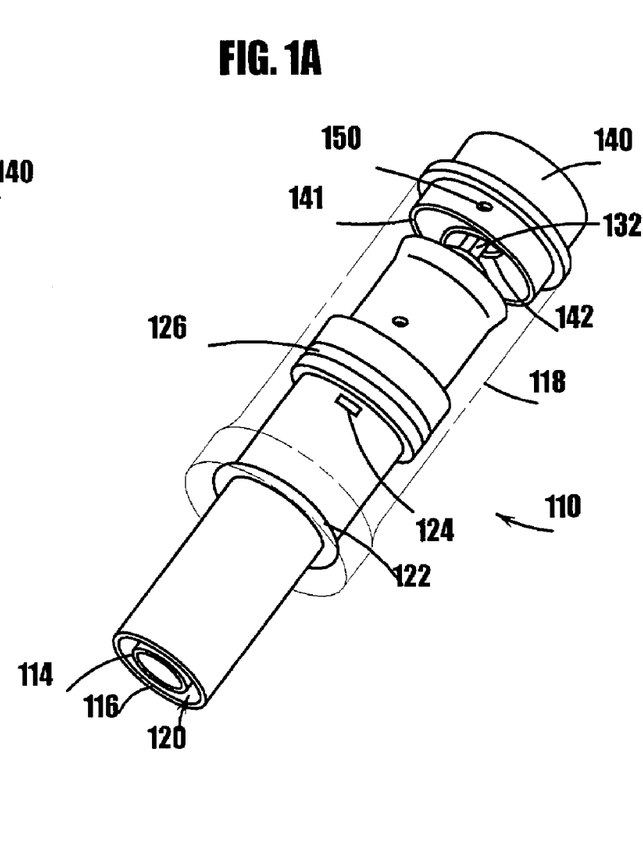
FIG. 1A is a perspective view of a device for injecting a substance intradermally in accordance with subject invention, and in particular the housing of the device is shown in phantom lines.
Figure 1B:
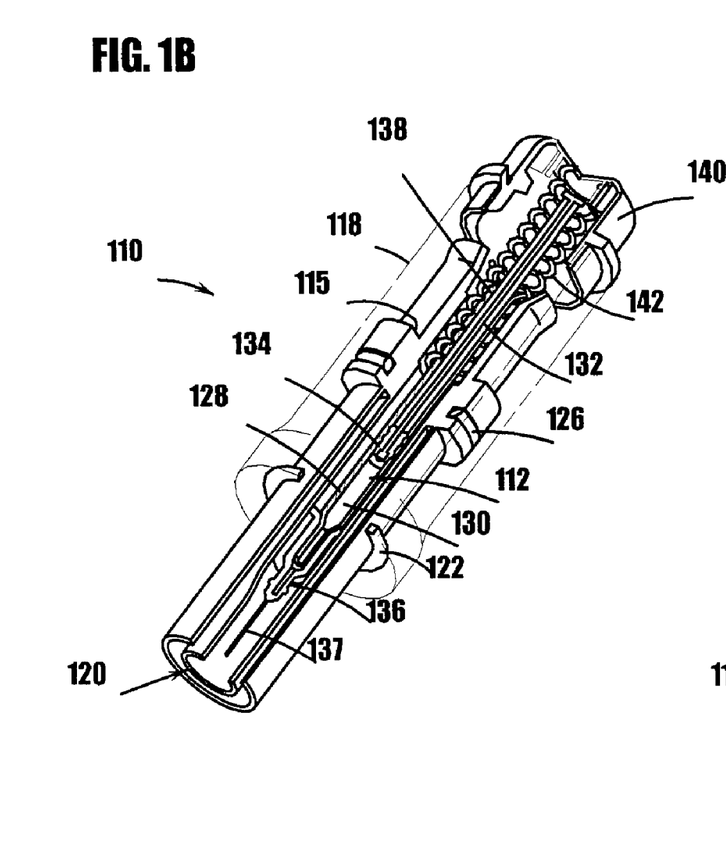
FIG. 1B is a perspective, partial cross-sectional view of the device of FIG. 1A.
Figure 1C:
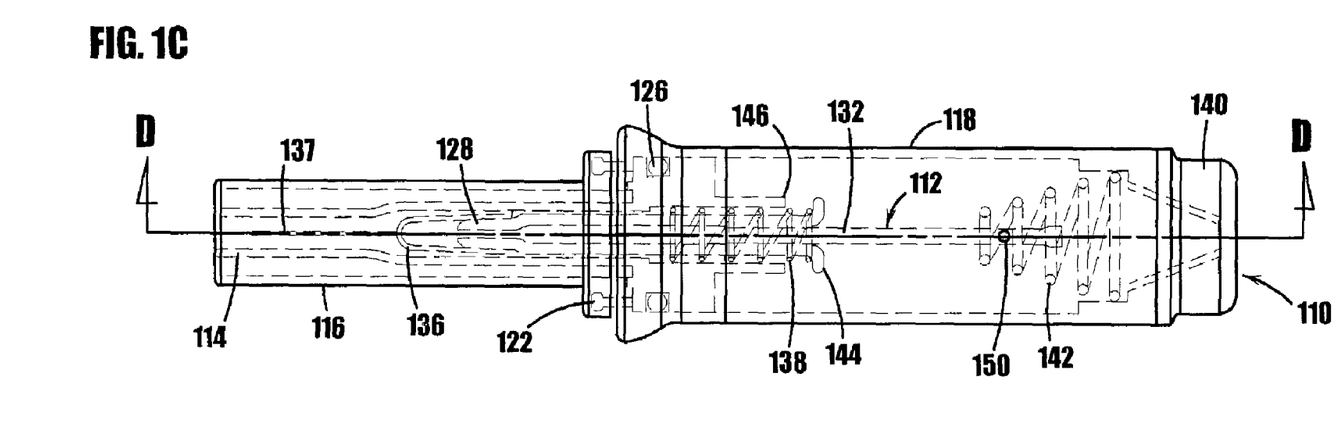
FIG. 1C is a plan, line view of the device of FIG. 1A.
Figure 1D:
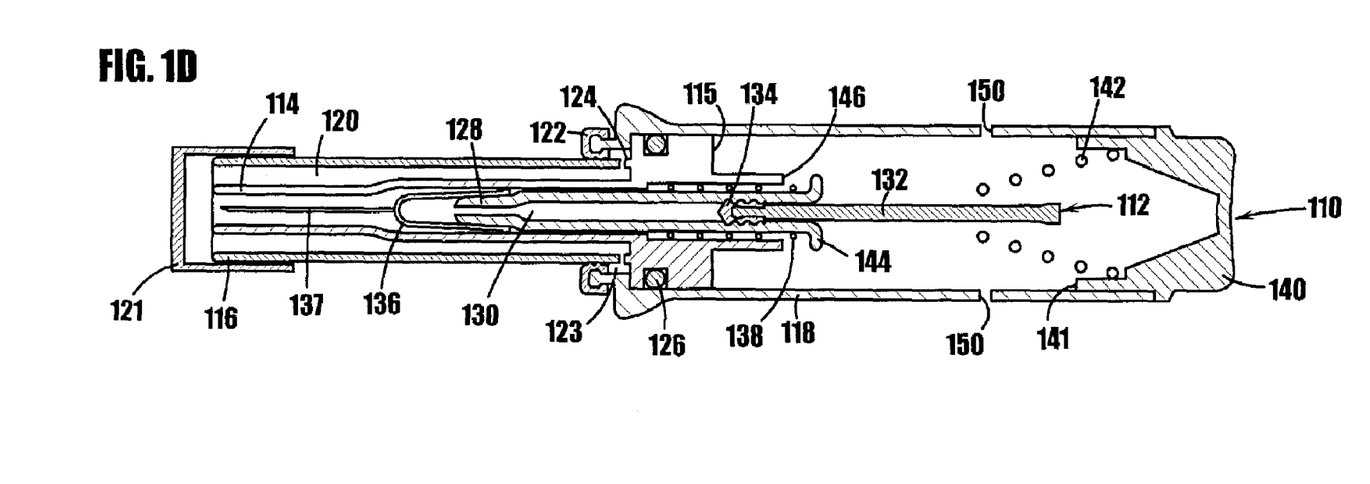
FIG. 1D is a cross-sectional view of the device of FIG. 1C taken along line D—D.
Figure 2A:
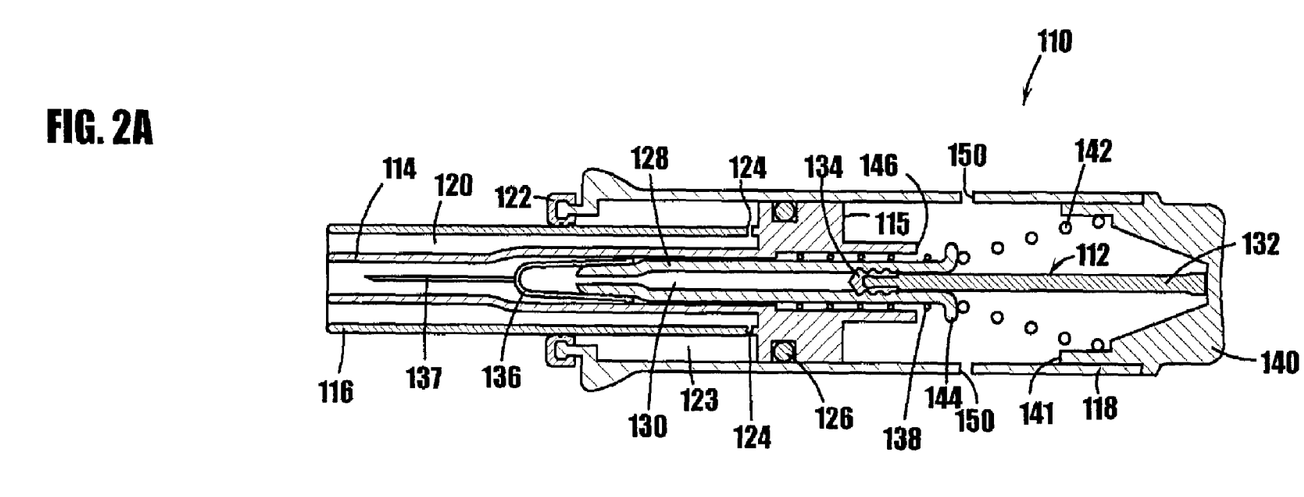
FIGS. 2A–D are cross-sectional views of the device of FIG. 1A in various positions during injection of a substance.
Figure 2B:
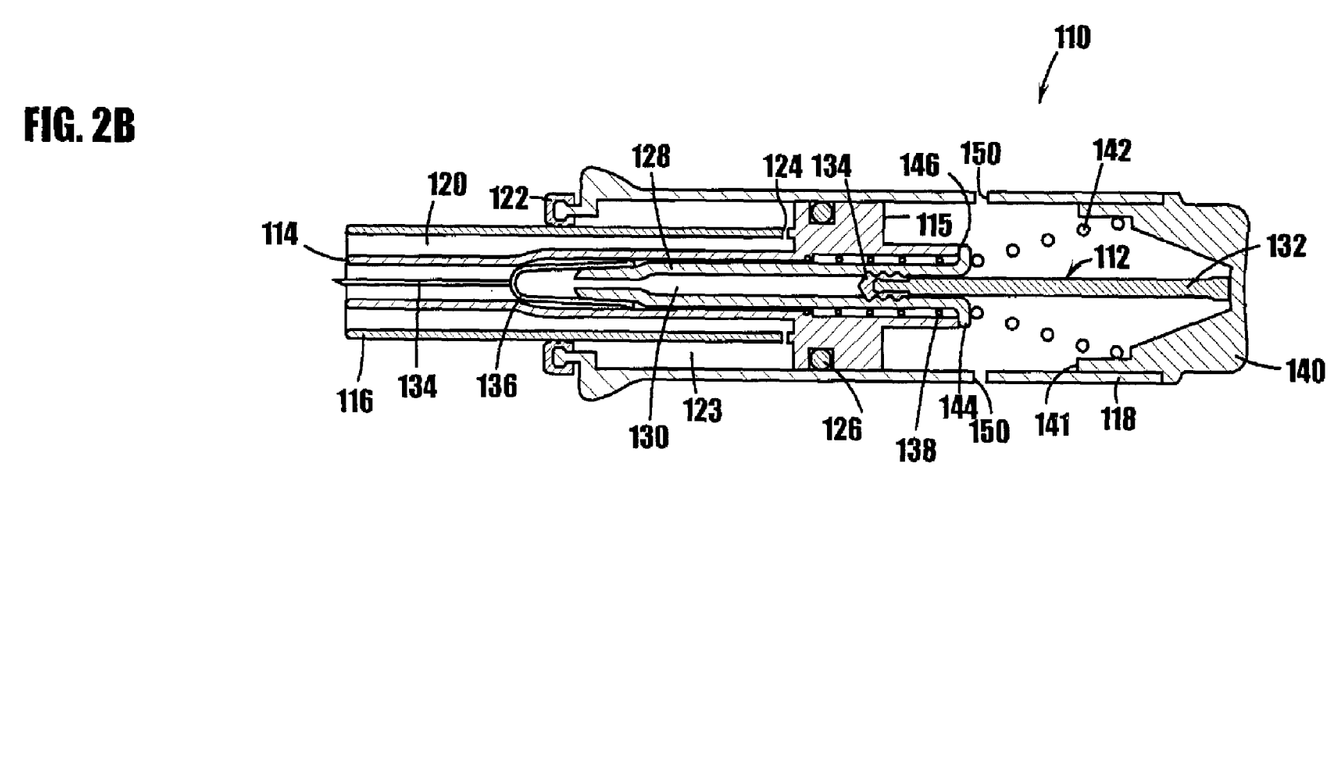
Figure 2C:
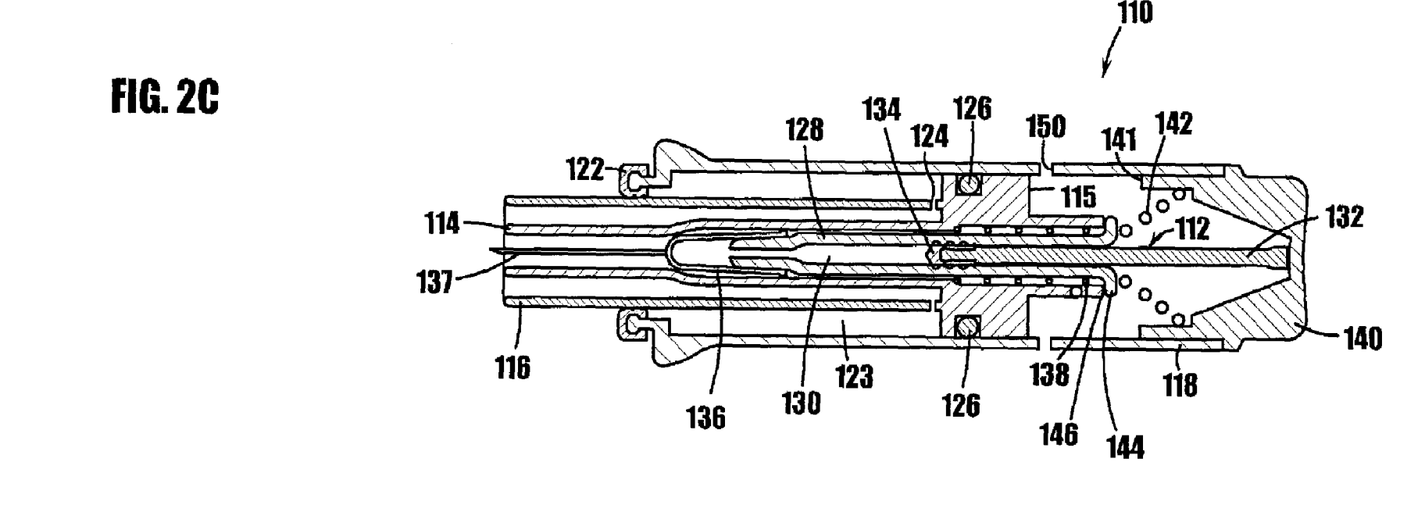
Figure 2D:
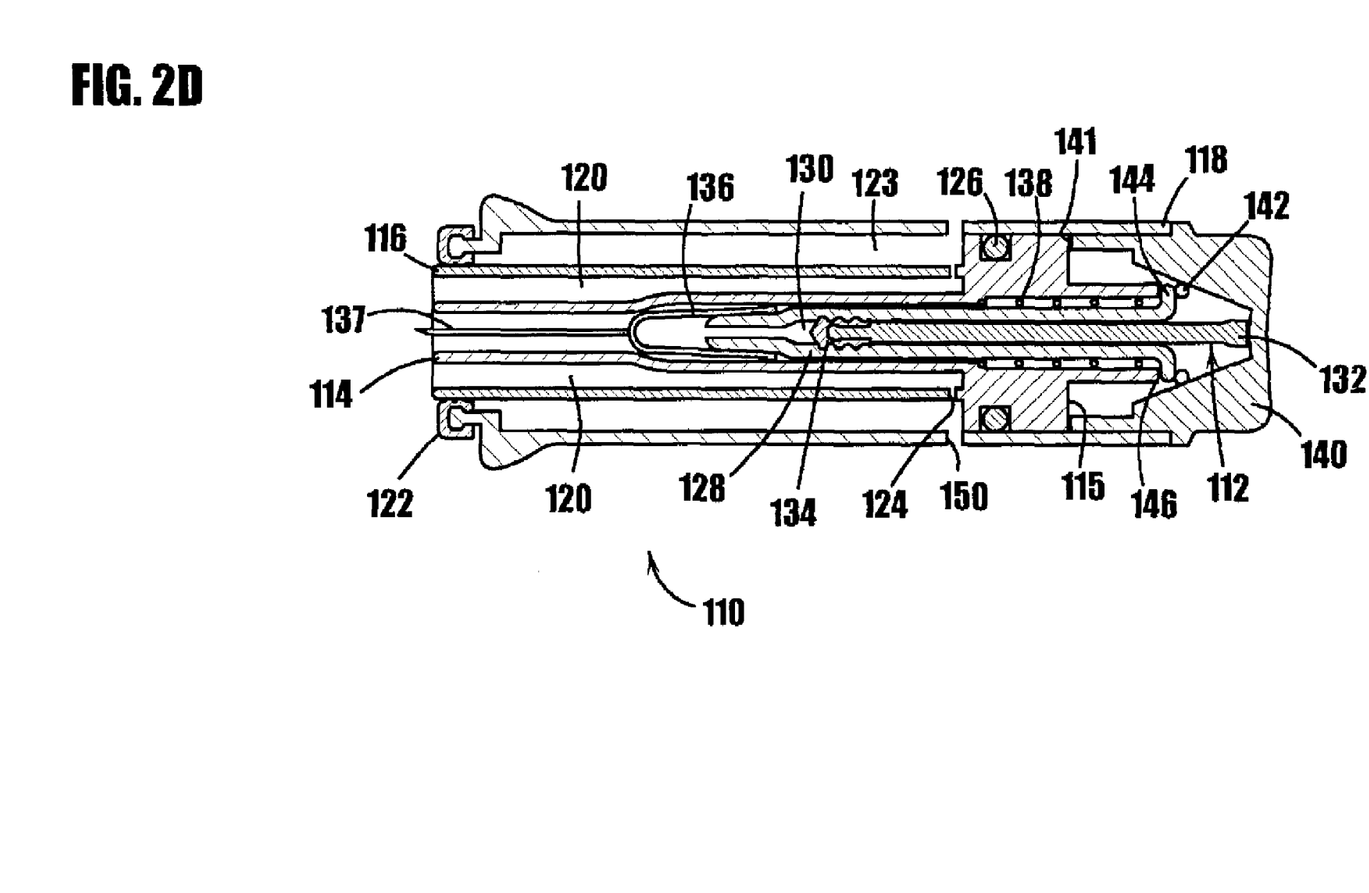
Figure 3:
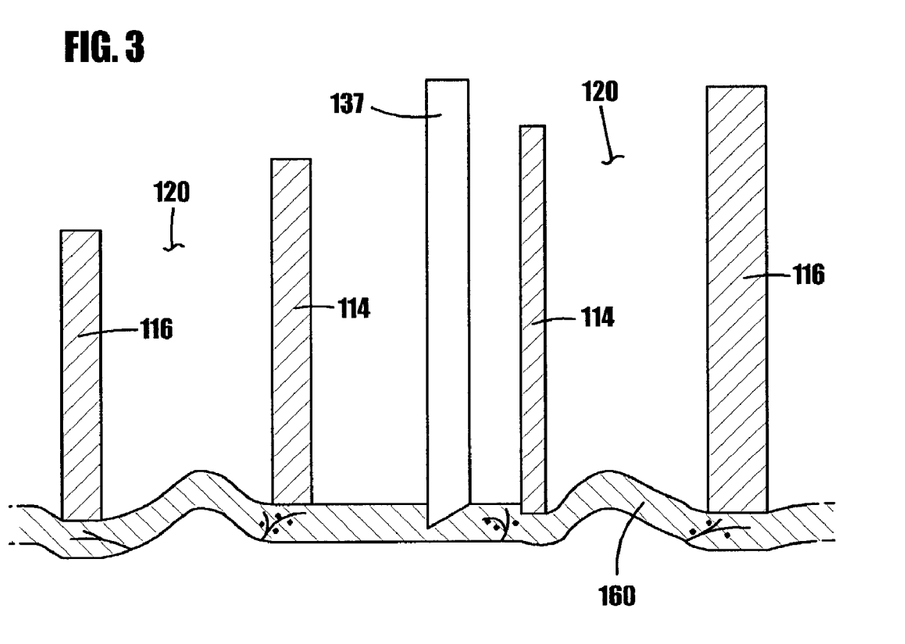
FIG. 3 is an enlarged localized cross-sectional view of the needle of the device of FIG. 1A penetrating the skin.

Referring to FIGS. 1D through 3, in operation, the safety cap 121 is removed, and the inner shell 114 and the outer shell 116 are placed against the skin 160 of the patient (FIG. 3). As the cap 140 is depressed, the variable length channel 123 expands to create a vacuum. The vacuum extends into the annular channel 120 through ports 124. As shown in FIG. 3, the vacuum pulls the surface of the skin 160 into the channel 120. As a result, the skin 160 is stretched tightly over the inner shell 114. The folds and contours of the skin 160 along with tissue compliance, which can make penetration to a fixed depth difficult, are effectively and painlessly removed. Such tensioning results in the target area of the skin surface being a substantially flat, taut reference plane. The skin tensioning also helps to ensure that the cannula 137 will always penetrate at a predetermined fixed angle with respect to the reference plane of the skin. As shown in FIG. 3, the cannula 137 penetrates at an approximately 90° angle. The syringe 112 preferably has an angled tip cannula 137.

As best seen in to FIGS. 2A through 2D, as the cap 140 is depressed, the housing 118 slides down the outer shell 116 and the spring 142 engages the flange 144 on the body 128, at approximately the same time the cap 140 contacts the plunger 132. The spring 138 biasing the body 128 is softer than the spring 142 attached to the cap and, thus, the spring 138 compresses before the spring 142 begins to compress. As the cap 140 is depressed further, the softer spring 138 significantly deforms until the flange 144 makes contact with a hard stop 146, as best shown in FIG. 2B. The hard stop 146 limits the distance which the syringe 112 extends. As a result, the cannula 137 of the syringe 112 penetrates the skin 160 to the same predetermined depth during each use. Preferably, the hard stop 146 is integral with the inner shell 114 and configured to allow the needle syringe 112 to extend 1.5 mm. The medicament is not expelled before complete insertion of the cannula 137 to the predetermined depth.

As best seen in FIGS. 2B through 2D, as the cap 140 is continued to be depressed, the spring 142 begins to deform and the plunger 132 is inserted into the cavity 130 of the syringe 112. As a result, the plunger 132 expels the dosage out of the needle portion 136 into the skin 160 of the patient. The insertion of the plunger 132 into the syringe body 128 is limited by a sleeve 141 of the cap 140 contacting a shoulder 115 formed by the inner shell 114, as best seen in FIG. 2D. Preferably, the sleeve 141 and shoulder 115 are sized and configured to determine the dosage of substance released from the syringe 112. At the end of the stroke of the cap 140, a plurality of relief holes 150 formed in the housing 118 vent the variable length channel 123 to ambient and, in turn, release the vacuum on the skin 160 to allow removal of the device 110. In another embodiment, the relief holes 150 are omitted to create a pneumatic return spring as the housing 118 naturally retracts from the two shells 114, 116. Once the cap 140 is released, the spring 138 provides a return force for automatic withdrawal of the needle portion 136. Thus, the device 110 operates in one single motion which can be performed without the aid of a second person. In order to prepare for another injection, the cap 140 is removed from the housing 118. The used needle syringe 112 is removed and replaced with a new full needle syringe 112.

Figure 4A:
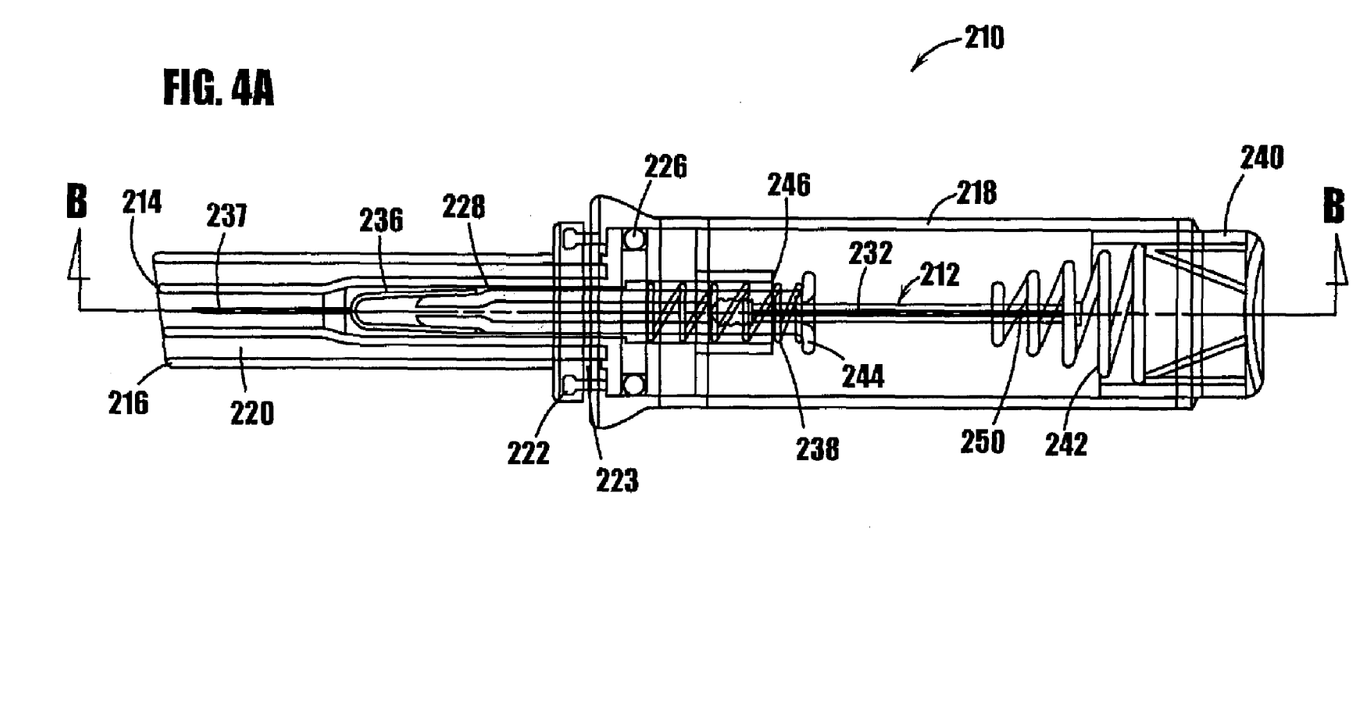
FIG. 4A is a plan, line view of another device for injecting a substance intradermally in accordance with subject invention.
Figure 4B:
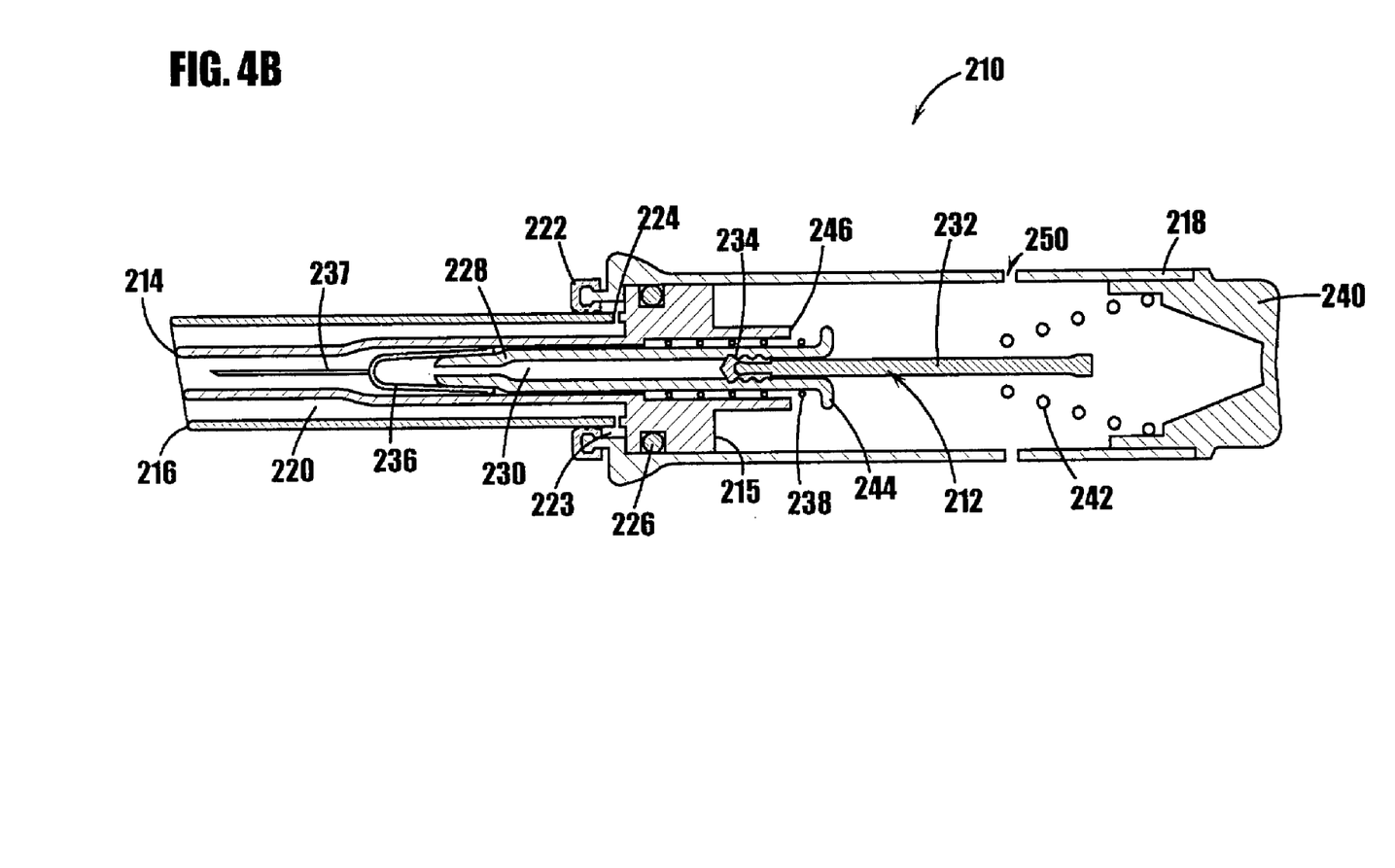
FIG. 4B is a cross-sectional view of the device of FIG. 4A taken along line B—B.
Figure 5:
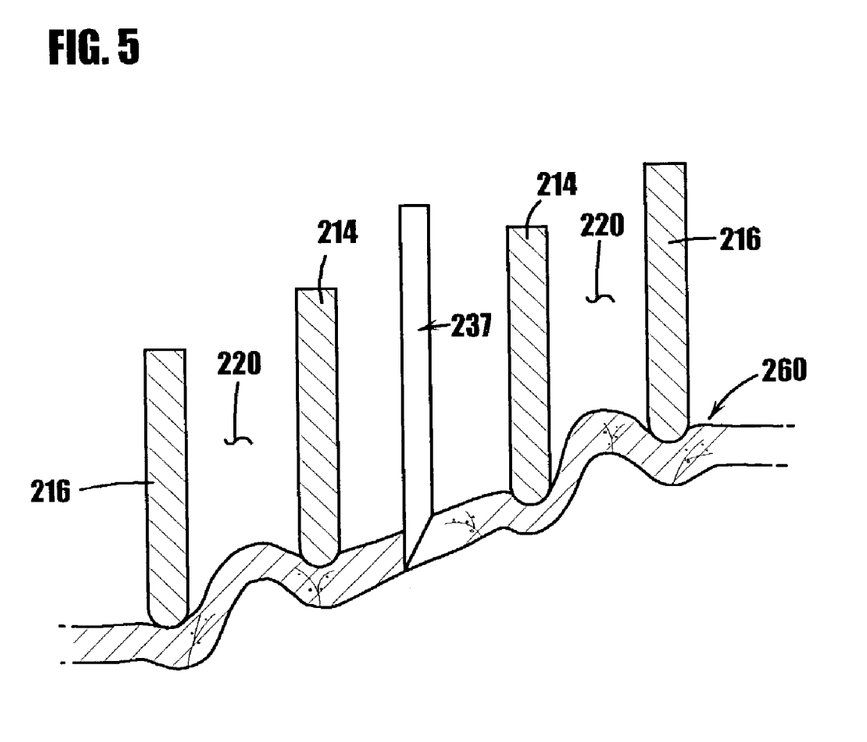
FIG. 5 is an enlarged localized cross-sectional view of the needle of the device of FIG. 4A penetrating the skin.

Referring to FIGS. 4A, 4B and 5, a device 210 has a single relief hole 250 formed in the shell 218 and shells 214, 216 with the distal ends angled with respect to the axis of the device 210. As will be appreciated by those of ordinary skill in the pertinent art, the device 210 utilizes the same principles of the device 110 described above. Accordingly, like reference numerals preceded by the numeral "2" instead of the numeral "1" are used to indicate like elements. The inner shell 214 and outer shell 216 form a channel 220 for tensioning the skin 260 of the patient by vacuum. Introduction of the cannula 237 at an angle to the skin 260 increases the effective allowed needle bevel, decreasing the apparent cross-sectional area of the cannula 237 and sensation to the patient. As a result of the angle, a larger area aperture at the end of the cannula 237 can be used to increase the total drug volume that can be dispensed. The needle portion 236 has an angled needle tip which forms a complementary angle preferable with the skin 260 when stretched across the inner shell 114. In another embodiment, the cannula 237 has a flat needle tip and the shells 214, 216 still create an angled target area of skin 260. Preferably, the angle or lack thereof of the cannula 237 corresponds to the angle of the distal end of the concentric shells 214, 216.

Figure 6A:
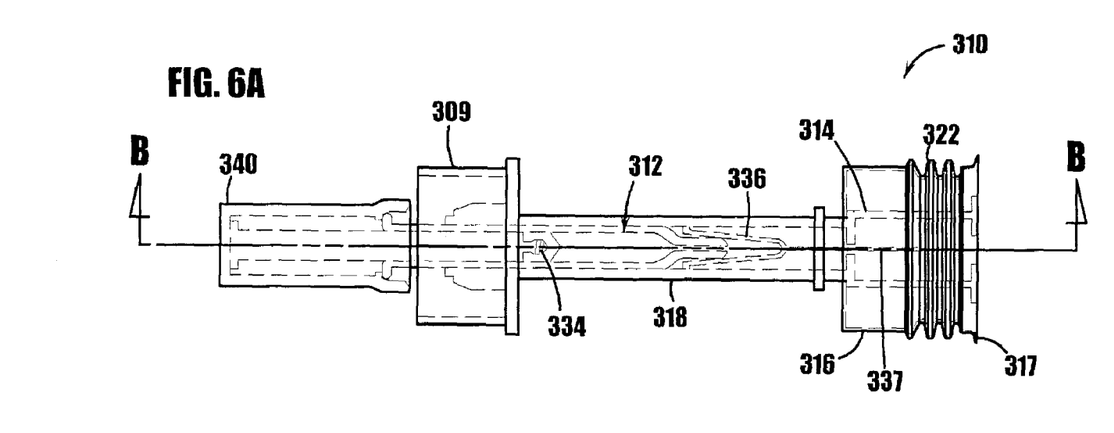
FIG. 6A is a plan, line view of still another device for injecting a substance intradermally in accordance with subject invention.
Figure 6B:
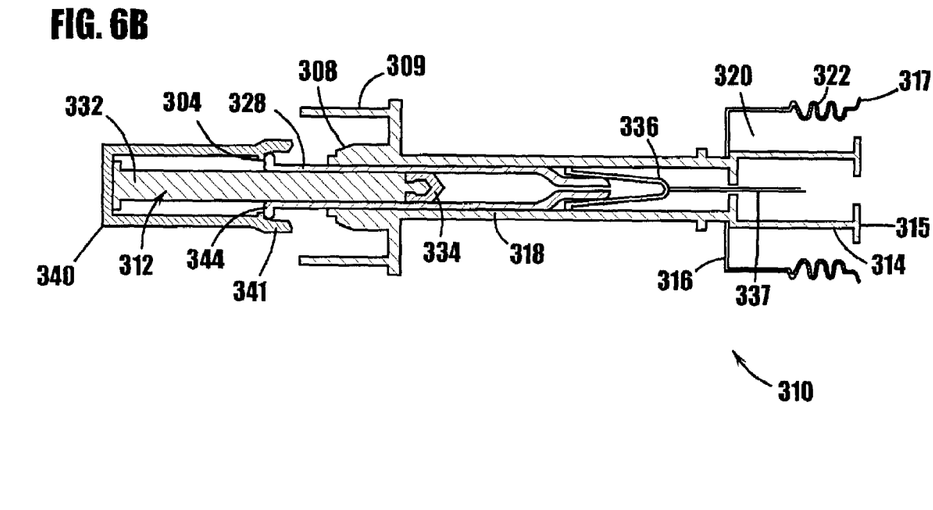
FIG. 6B is a cross-sectional view of the device of FIG. 6A taken along line B—B.

Referring to FIGS. 6A and 6B, another embodiment of a device for intradermal delivery of substances is referred to generally by reference numeral 310. As will be appreciated by those of ordinary skill in the pertinent art, the device 310 utilizes the same principles of the devices 110, 210 described above. Accordingly, like reference numerals preceded by the numeral "3" instead of the numerals "1" or "2" are used to indicate like elements. Tensioning of the patient's skin across inner shell 314 is utilized to provide a substantially flat target area of skin for penetration by the cannula 337 of the needle portion 336. The skin is tensioned by the combination of vacuum generated by the outer shell 316 and the outer shell 316 engaging the skin and radially expanding.

The device 310 consists of a syringe 312 slidably received within a housing 318. At a distal end, the cannula 337 of the syringe 312 nests inside the inner shell 314 which is surrounded by the outer shell 316. A sealing surface 315 on the inner shell 314 and a sealing lip 317 on the outer shell 316 provide for substantially airtight engagement with the skin of the patient. The proximal end of the housing 318 forms a camming surface 308 surrounded by a protective sleeve 309. A portion of the syringe body 328 and plunger 332 extend out of the housing 318. A cap 340 has deflectable ears 341 for engaging the body 328 of the syringe 312 and the camming surface 308 of the housing 318. The flange 344 of the syringe body 328 is effectively captured between the inner deflectable ears 341 and an annular protrusion 304 of the cap 340.

In operation, the shells 314, 316 are manually depressed against the skin to create a substantially airtight seal between the skin and the sealing surface 315 and sealing lip 317. As the shells 314, 316 are depressed further, the sealing lip 317 expands radially outward and, in turn, stretches the skin across the inner shell 314. The radial expansion is also facilitated by bellows 322 in the outer shell. As a further result of the radial expansion of the outer shell 316, a vacuum is generated in the channel 320 between the inner shell 314 and outer shell 316. The vacuum pulls the skin into the channel 320 to further tension the skin across inner shell 314 and create a substantially taut target area of skin. In an alternate embodiment, microholes are provided in the outer shell 316 to prevent vacuum accumulation therein.

Once tensioned against the skin, the cap 340 is depressed to slide the syringe 312 within the housing 318 and thereby insert the cannula 337 to the desired depth. The insertion depth of the cannula 337 is limited by the flange 344 of the syringe body 328 contacting the camming surface 308. The deflectable ears 341 of the cap 340 also engage the camming surface at approximately the same time. As the cap 340 is continued to be depressed, camming surface 308 forces radial expansion of the deflectable ears 341 and the cap 340 slides over the syringe body 328 to force the plunger 332 into the syringe body 328 and, in turn, deliver the substance into the skin of the patient. In another embodiment, the cap 340 has limited travel between the camming surface 308 and protective sleeve 309 which serves to control the quantity of substance delivered during injection.

While the invention has been described with respect to preferred embodiments, those skilled in the art will readily appreciate that various changes and/or modifications can be made to the invention without departing from the spirit or scope of the subject invention as defined by the appended claims.

What is claimed is:

1. A delivery device comprising:
   a housing including a base defining a first skin-engaging surface portion forming a needle aperture and defining a substantially planar target penetration region of skin, and a second skin-engaging surface portion extending radially relative to the first skin-engaging surface portion to substantially prevent relative movement of the skin and the base and releasably secure the base to the skin;
   a syringe including a syringe body coupled to the housing, a plunger slidably received within the syringe body and a needle in fluid communication with the syringe body, wherein the needle is movable through the needle aperture upon slidably moving the syringe through the housing to thereby insert the needle into the substantially planar target penetration region of the skin and inject a substance contained within the syringe; and
   at least one stop surface fixed relative to at least a portion of the first skin-engaging surface and adapted to cooperate with the syringe to limit a depth of insertion of the needle into the substantially planar target penetration region of the skin.

2. A delivery device as defined in claim 1, further comprising a vacuum chamber in fluid communication with the base for drawing a vacuum within the base and, in turn, releasably securing the first and second skin-engaging surfaces to the skin.

3. A delivery device as defined in claim 1, wherein the depth is such that an opening of the needle is located substantially entirely within the skin.

4. A delivery device as defined in claim 1, wherein the needle has an angled needle tip.

5. A delivery device as defined in claim 1, wherein the substantially planar target penetration region is oriented at an acute angle relative to an axis of the delivery device.

6. A delivery device as defined in claim 5, wherein the acute angle is within the range of about 30° to about 60° relative to the axis of the intradermal delivery device.

7. A delivery device as defined in claim 1, wherein the housing includes first and second parts, and at least one of the first and second parts is movable relative to the other.

8. A delivery device as defined in claim 1, wherein the base of the housing includes an inner shell defining the first skin-engaging surface and an outer shell surrounding the inner shell defining the second skin-engaging surface.

9. A delivery device as defined in claim 1, further comprising a mechanism associated with the housing for generating vacuum.

10. A delivery device as defined in claim 9, wherein the mechanism for generating vacuum includes an outer shell substantially concentric with an inner shell defining an elongated annular channel therebetween, and the housing defines a sealed channel of variable size in communication with the elongated annular channel such that in a retracted position the shells are placed against a patient's skin and the housing slides to increase the sealed channel in size, thereby creating a vacuum within the elongated annular channel and, in turn, tensioning the patient's skin across the inner shell such that the substantially planar target penetration region is established.

11. A delivery device as defined in claim 10, further comprising a relief opening for porting the sealed chamber to ambient conditions in an extended position.

12. A delivery device as defined in claim 1, further comprising a stop connected to the housing for controlling a dosage of substance released from the syringe.

13. A method for delivering a substance into a patient comprising the steps of:
(a) providing a delivery device including a housing having a base defining a first skin-engaging surface portion forming a needle aperture and defining a substantially planar target penetration region of skin, and a second skin-engaging surface portion extending radially relative to the first skin-engaging surface portion to substantially prevent relative movement of the skin and the base, and releasably secure the base to the skin;
(b) reciprocally mounting a syringe in the housing, the syringe having a syringe body for storing a substance, a plunger slidably received within the syringe body and a needle in fluid communication with the syringe body;
(c) releasably securing the first and second skin-engaging surface portions on the skin of the patient;
(d) forming the substantially planar target penetration region of the skin;
(e) inserting the needle of the syringe into the substantially planar target penetration region of the skin upon slidably moving the syringe through the housing;
(f) controlling a depth of insertion of the needle into the substantially planar target penetration region with at least one stop surface fixed relative to at least a portion of the first skin-engaging surface for determining the depth in cooperation with the syringe; and
(g) injecting the substance from the syringe body through the needle into the patient.

14. A method as defined in claim 13, further comprising the step of creating a vacuum between the first and second skin-engaging surface portions to form the substantially planar target penetration region of the skin.

15. A method as defined in claim 13, further comprising the step of inserting the needle at a predetermined acute angle between the axis of the needle and the substantially planar target penetration region of the skin.

16. A method as defined in claim 13, wherein the step of forming a substantially planar target penetration region on the skin includes tensioning the skin.

17. A delivery device comprising:
first means for defining a substantially planar target region of skin;
second means for releasably securing the first means to the skin and preventing relative movement of the substantially planar target region of the skin and the first means;
third means for storing a substance to be injected into the skin;
fourth means for releasing the substance from the third means;
fifth means in fluid communication with the third means for penetrating the substantially planar target region of the skin and injecting the substance contained within the third means; and
sixth means fixed relative to the first means for limiting a depth of insertion of the fifth means.

18. A delivery device as defined in claim 17, wherein the first means is defined by a first skin-engaging surface portion for engaging the skin and defining the substantially planar target penetration region of skin, and forming an aperture for receiving the fifth means therethrough.

19. A delivery device as defined in claim 17, wherein the second means is defined by a second skin-engaging surface portion extending radially relative to the first means, for engaging the skin and preventing relative movement of the skin and the first means.

20. A delivery device as defined in claim 19, further comprising a vacuum chamber formed adjacent to the second skin-engaging surface portion and connectable in fluid communication with the skin to releasably secure the second skin-engaging surface to the skin.

21. A delivery device as defined in claim 17, wherein the third means is defined by a chamber of a syringe.

22. A delivery device as defined in claim 17, wherein the fourth means is defined by a plunger slidably received within the third means.

23. A delivery device as defined in claim 17, wherein the fifth means is a cannula.

24. A delivery device as defined in claim 17, wherein the sixth means is at least one stop surface sized and configured to limit a depth of insertion of the fifth means.

25. A delivery device as defined in claim 17, wherein the depth of insertion is such that a release aperture of the fifth means is located substantially entirely within the skin.

26. A delivery device as defined in claim 17, wherein the substantially planar penetration region is oriented at an acute angle relative to an axis of the delivery device.

27. A delivery device as defined in claim 1, wherein the at least one stop surface is arranged so the the depth of insertion of the needle allows for an intradermal injection.

* * * * *